US005239095A

United States Patent [19]

Bade

[11] Patent Number: 5,239,095

[45] Date of Patent: Aug. 24, 1993

[54] METHOD FOR THE PREPARATION OF FLOWABLE, AQUEOUS DISPERSIONS OF BETAINES

[75] Inventor: Volkbert Bade, Essen, Fed. Rep. of Germany

[73] Assignee: Th. Goldschmidt AG, Essen, Fed. Rep. of Germany

[21] Appl. No.: 786,037

[22] Filed: Oct. 31, 1991

[30] Foreign Application Priority Data

Dec. 20, 1990 [DE] Fed. Rep. of Germany ....... 4040887

[51] Int. Cl.$^5$ .......... C07C 231/14

[52] U.S. Cl. .......... 554/69; 554/41; 554/59; 554/68; 564/296

[58] Field of Search .......... 260/404.5; 252/153, 252/351, 142; 584/56, 166; 554/64, 68; 564/296

[56] References Cited

U.S. PATENT DOCUMENTS 3,225,074 12/1965 Cowen .......... 260/404.5
4,861,517 8/1989 Bade .......... 252/546

FOREIGN PATENT DOCUMENTS 2022125 12/1979 United Kingdom .

OTHER PUBLICATIONS

Chemical Abstracts, vol. 97, #81, 1982, 575024.

*Primary Examiner*—José G. Dees
*Assistant Examiner*—Deborah D. Carr
*Attorney, Agent, or Firm*—Anderson Kill Olick & Oshinsky

[57] ABSTRACT

A method is disclosed for the preparation of flowable, aqueous dispersions, which contain 10 to 30% by weight of betaines of the general formula

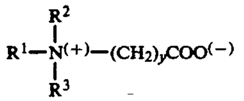

wherein $R^1$ is a linear alkyl group with at least 16 carbon atoms or the $R^4CONH(CH_2)_x$— group, in which $R^4CO$ is an acyl group derived from a saturated, linear fatty acid with at least 16 carbon atoms and $x=2$ or 3, $R^2$, $R^3$ are the same or different and in each case represent an alkyl group with 1 to 4 carbon atoms, y is 1, 2 or 3, by quaternizing a tertiary amine of the general formula $R^1—NR^2R^3$ with ω-halogenalkylcarboxylic acids $X(CH_2)_yCOOY$ or their salts (X=halogen group, Y=hydrogen, alkali or ammonium) in an aqueous or alcoholic, aqueous solution at elevated temperature. Anionic surfactants are added to the reaction mixture before the quaternization reaction in such amounts, that the ultimate dispersion contains 1 to 10% by weight of anionic surfactants.

White, flowable, dispersions, which can be handled, pumped and metered out well are obtained.

4 Claims, No Drawings

METHOD FOR THE PREPARATION OF FLOWABLE, AQUEOUS DISPERSIONS OF BETAINES

FIELD OF INVENTION

The invention generally relates to betaines and is particularly directed to a method for the preparation of flowable, aqueous dispersions containing 10 to 30% by weight of betaines of the general formula

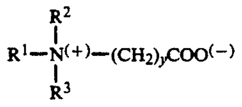

I wherein $R^1$ is an alkyl group with at least 16 carbon atoms or the $R^4CONH(CH_2)_x$— group, in which $R^4CO$ is an acyl group derived from a saturated fatty acid with at least 16 carbon atoms and $x=2$ or 3, $R^2$, $R^3$ are the same or different and in each case represent an alkyl group with 1 to 4 carbon atoms, y is 1, 2 or 3, by quaternizing a tertiary amine of the general formula $$R^1—NR^2R^3 \qquad II$$

with ω-halogenalkylcarboxylic acids $X(CH_2)_yCOOY$ or their salts (X=halogen group, Y=hydrogen, alkali or ammonium) in an aqueous or aqueous-alcoholic solution at elevated temperatures.

BACKGROUND INFORMATION AND PRIOR ART

Betaines of the aforementioned formula, in which $R^1$ is an alkyl group with 8 to 14 carbon atoms or the $R^4CO$ group of which is an acyl group of a fatty acid with 8 to 12 carbon atoms, have increasingly gained in importance in recent years as cleansing agents for the body. They combine excellent cleansing properties with good skin compatibility. In aqueous solution, the betaines form a stable, thick foam, which does not collapse even in the presence of soap.

The synthesis of betaines is described in many patents, of which U.S. Pat. No. 3,225,074 is named as a representative. The appropriate tertiary amine of the general formula II is usually reacted for this purpose with the alkali salt of an ω-halogencarboxylic acid, usually, the sodium salt of chloroacetic acid. The reaction preferably takes place in an aqueous medium. The alkali chloride, formed during the reaction, remains in the solution and is not removed.

The betaines of the state of the art are mostly marketed in the form of their 30% by weight aqueous solutions. These betaines are essentially those obtained by the quaternization of fatty alkyl dialkylamines or fatty acid amideamines, the fatty alkyl or fatty acid groups of which, on the average, having 12 to 14 carbon atoms. The longer the chain length of the alkyl group or of the fatty acid mixture used for the synthesis of the betaine, the greater is the increase in the viscosity of the betaine solutions with increasing concentration. It was therefore in the past only possible to prepare aqueous solutions of low concentration, such as 2 to 5% by weight of betaine, from betaines, the $R^4CO$ acyl group of which is derived from higher molecular weight fatty acids, such as stearic acid.

It is known from the art that the viscosity of betaine solutions can be lowered by aiming for the formation of an aqueous phase with a lamellar structure, a so-called G phase, by the addition of other surfactants. British patent application 2,022,125 A may be mentioned in this context, which relates to a method for producing a concentrated, aqueous, surface-active preparation, which contains, as active component, a mixture of at least two surface active substances, which are not homologous and each of which is present in an amount of at least 5%, based on the mixture. The mixture is capable of forming a liquid G phase. At least one of the surface active substances can be synthesized from a precursor by a reaction in an aqueous solution. Under the reaction conditions, this precursor is a liquid and does not bring about a significant decomposition of the other surface active substance in the mixture. The preparation is formed by converting at least one of the precursors into the corresponding surface active substance in the presence of at least one of the other surface active substance components and carrying out this conversion in the presence of amounts of water, sufficient to keep the reaction mixture in a liquid state and to obtain a final preparation, which is present at least predominantly in the G phase.

This method can best be illustrated by means of an example. In Example 2 of the British patent application 2,022,125 A, 797 g of a 70% solution of a sodium ether lauryl sulfate, which is present in the G phase, is heated together with 442 g of a $C_{12}/C_{14}$-alkyldimethylamine and 209 g of chloroacetic acid in 140 g of water, the pH of the mixture being maintained at $7.8\pm0.2$ by the addition of sodium hydroxide solution. The betaine is thus synthesized here in the presence of an alkyl ether sulfate. The product contains 63% of a surface active substance, the ratio by weight of betaine to anionic surfactant being 1:1. The product is liquid and is present in the G phase.

However, this method cannot be employed with betaines, the $R^1$ alkyl group or the $R^4CO$ acyl group of which contains 16 or more carbon atoms. With these products in an aqueous medium with anionic surfactants in the concentration ranges given, lamellar structures, which are present in the G phase, are not formed.

OBJECT OF THE INVENTION

It is thus the primary object of the invention to provide a method of producing flowable, pourable and thus meterable aqueous preparations even of betaines of the general formula I, the $R^1$ or $R^4CO$ group of which has 16 or more carbon atoms.

Generally, it is an object of the invention to improve on the art of preparing betaine preparations.

SUMMARY OF THE INVENTION

Pursuant to the inventive method, which is characterized in that anionic surfactants are added in such amounts to the reaction mixture before the quaternization reaction, that the finished solution contains about between 1 to 10% by weight of anionic surfactants.

The finished solution preferably contains 2 to 5% by weight of anionic surfactants.

An aqueous betaine dispersion is obtained by the inventive method. The betaine accordingly is present in the form of small particles as external phase in the dispersion. Compared to a product with a lamellar G phase, the following are some of the differences that exist.

| Inventive Product | Dispersion with G Phase |
|---|---|
| white dispersion | transparent to slightly cloudy gel |
| stable over a wide range of concentrations | stable G phase only within a very narrow range of concentrations |
| shows behavior of a Newtonian liquid | shows behavior of a thixotropic gel |

In the case of the inventive method, a different state of the aqueous preparation is thus attained than is the state of the preparation of British patent application 2,022,125 A. Moreover, it could not have been foreseen or predicted in any way that, instead of the liquid, lamellar G phase, a dispersion with a different viscosity behavior would be produced with betaines of the general formula I and having a longer carbon chain.

Particularly preferred for the inventive method ar tertiary amines, the $R^1$ group of which is an alkyl group with 18 to 22 carbon atoms. The same is true for the $R^4$ group.

The $C_{18}H_{36}$—, $C_{20}H_{22}$— and $C_{22}H_{25}$— groups are therefore particularly preferred as $R^1$ groups and the acyl groups of stearic, arachidic and behenic acids are particularly preferred as $R^4CO$— groups.

Particularly preferred as anionic surfactants are the alkali, ammonium or amine salts of alkyl sulfates, alkyl ether sulfates, alkylarylsulfonates, α-olefinsulfonates or of the hemiesters of sulfosuccinic acid. Examples of these are lauryl sulfate, polyoxyethylene-3-lauryl ether sulfate and sodium dodecylbenzylsulfonate. They are used in concentrations of about between 1 to at most 5% by weight, based on the preparation.

A typical preparation, obtained by the inventive method, has the following composition:

| | |
|---|---|
| betaine* | 22.8% by weight |
| sodium lauryl ether sulfate | 3.5% by weight |
| sodium chloride | 3.4% by weight |
| glycolic acid | 0.3% by weight |
| water | 70.0% by weight |
| | 100.0% by weight |

*$R^1 = C_{17}H_{35}CONH(CH_2)_3$—; $R^2$, $R^3 = CH_3$; y = 1

The product is a white, flowable dispersion with a viscosity of 3,000 to 5,000 mPas at 25° C.

The inventive method and the properties of the products obtained with it will be illustrated in greater detail by the following examples, it being understood that these examples are given by wa of illustration and not by way of limitation.

EXAMPLE 1

The following are weighed into a 500 mL 3-neck flask, which is equipped with a stirrer, thermometer and reflux condenser:

| | |
|---|---|
| 36.8 g (0.1 moles) | the dimethylaminopropylamide of stearic acid |
| 12.8 g (0.11 moles) | sodium monochloroacetate |
| 23.2 g | sodium lauryl ether sulfate (28% by weight in water), 6.5 g of 100% by weight |
| 124.0 g | water. |

This mixture is allowed to react for 10 hours at 95° to 98° C. with stirring and then cooled.

A flowable, white dispersion (186.3 g) of the following composition is obtained:

| | |
|---|---|
| 42.6 g betaine stearate = | 22.8% by weight |
| 6.5 g sodium lauryl ether sulfate = | 3.5% by weight |
| 6.5 g sodium chloride = | 3.5% by weight |
| 130.7 g water = | 70.2% by weight |

The viscosity of the dispersion at room temperature is 3,000 mPas.

EXAMPLE 2

The following are weighed into a 500 mL 3-neck flask, which is equipped with a stirrer, thermometer and reflux condenser:

| | |
|---|---|
| 36.8 g | the dimethylaminopropylamide of stearic acid |
| 12.8 g | sodium monochloroacetate |
| 13.4 g | sodium lauryl ether sulfate (28% by weight in water) |
| 124.0 g | water. |

This mixture is allowed to react for 10 hours at 95° to 98° C. and then cooled.

A flowable, white dispersion (187 g) of the following composition is obtained:

22.9% by weight betaine stearate
2.0% by weight sodium lauryl ether sulfate
3.5% by weight sodium chloride
71.6% by weight water The viscosity of the dispersion at room temperature is ≈4,000 mPas.

EXAMPLE 3

In an experiment similar to that of Example 2, the amount of sodium lauryl ether sulfate (100% by weight) is increased to 5% by weight of the formulation, the other conditions being kept the same.

A flowable, white dispersion of a betaine stearate of the following composition is likewise obtained:

22.9% by weight betaine stearate
5.0% by weight sodium lauryl ether sulfate
3.5% by weight sodium chloride
68.6% by weight water The viscosity of the dispersion at room temperature is ≈2,000 mPas.

In the following experiments, under conditions which are otherwise the same as in Example 1, 0.1 moles of the dimethylaminopropylamide of the corresponding fatty acid, 0.11 moles of sodium chloroacetate and 3.5% by weight of the respective surfactant (100% by weight) are used.

The experimental results ar shown in detail in the following Table.

TABLE

| Surfactant | $R^4$ = $C_{15}H_{31}CO$— | $C_{17}H_{35}CO$— | $C_{21}H_{43}CO$— |
|---|---|---|---|
| Sodium lauryl ether-3-sulfate | + | + | + |
| Dodecyl benzolsulfonate | + | + | + |

TABLE-continued

| Surfactant | $R^4 =$ $C_{15}H_{31}CO-$ | $C_{17}H_{35}CO-$ | $C_{21}H_{43}CO-$ |
|---|---|---|---|
| α-Olefinsulfonate | + | + | + |
| Sodium lauryl sulfate | + | + | + |
| Ammonium lauryl sulfate | + | + | + |
| Triethanolamine lauryl sulfate | + | + | + |
| Polyoxyethylene-8-stearate | – | – | – |
| Polyoxyethylene-20-stearate | – | – | – |
| Polyoxyethylene-40-stearate | – | – | – |
| Polyoxyethylene-4-lauryl ether | – | – | – |
| Polyoxyethylene-23-lauryl ether | – | – | – |
| Polyoxyethylene-10-stearyl ether | – | – | – |
| Polyoxyethylene-20-stearyl ether | – | – | – |
| Polyoxyethylene-20-sorbitol monolaurate | | | |
| Polyoxyethylene-4-sorbitol monolaurate | – | – | – |
| Polyoxyethylene-20-sorbitol monooleate | – | – | – |
| Polyoxyethylene-5-sorbitol trioleate | – | – | – |
| Polyoxyethylene-20-oleyl ether | – | – | – |

– = not flowable or gelled
\+ = flowable; 2000 to 5000 mPas

It is evident from the Table that the dispersions, obtained pursuant to the invention, are flowable. If the anionic surfactants are replaced by nonionic surfactants, products are obtained, which are no longer flowable or which have gelled.

I claim:

1. A method for the preparation of a flowable, aqueous dispersion, containing about between 10 to 30% by weight of betaines of the general formula

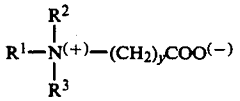

wherein $R^1$ is linear alkyl with at least 16 carbon atoms or $R^4CONH(CH_2)_x$—, in which $R^4CO$ is an acyl group derived from a saturated, linear fatty acid with at least 16 carbon atoms and x=2 or 3, $R^2$, $R^3$ are the same or different and in each case represent alkyl with 1 to 4 carbon atoms, and y is 1, 2 or 3, said method comprising quaternizing a tertiary amine of the general formula $$R^1—NR^2R^3$$

wherein $R^1$, $R^2$ and $R^3$ have the above meaning, with ω-halogenalkylcarboxylic acid, $X(CH_2)_yCOOY$ or its salts (X=halogen, Y=hydrogen, alkali or ammonium) in an aqueous or aqueous-alcoholic solution at elevated temperature, and adding anionic surfactant to the reaction mixture before the quaternization reaction in such amounts that the ultimate dispersion contains about between 1 to 10% by weight of anionic surfactant.

2. The method of claim 1, wherein anionic surfactant is added to the reaction mixture in such amounts that the ultimate dispersion contains about between 2 to 5% by weight of anionic surfactant.

3. The method of claims 1 or 2, wherein $R^1$ is either alkyl with 18 to 22 carbon atoms or $R^4CO$ is an acyl group of a fatty acid with 18 to 22 carbon atoms.

4. The method of claims 1 or 2, wherein the anionic surfactant is an alkali, ammonium or amine salt of alkyl sulfate, alkyl ether sulfate, alkylarylsulfonate, α-olefinsulfonate or hemiester of sulfosuccinic acid.

* * * * *